US010617788B2

United States Patent
McCoy

(10) Patent No.: US 10,617,788 B2
(45) Date of Patent: Apr. 14, 2020

(54) COLLAGEN PERMEATED MEDICAL IMPLANTS

(71) Applicant: McCoy Enterprises, LLC, Little Falls, NJ (US)

(72) Inventor: Annick F McCoy, Little Falls, NJ (US)

(73) Assignee: McCoy Enterprises, LLC, Little Falls, NJ (US)

(*) Notice: Subject to any disclaimer, the term of this patent is extended or adjusted under 35 U.S.C. 154(b) by 1011 days.

(21) Appl. No.: 14/607,484

(22) Filed: Jan. 28, 2015

(65) Prior Publication Data

US 2015/0209472 A1    Jul. 30, 2015

Related U.S. Application Data

(60) Provisional application No. 61/932,639, filed on Jan. 28, 2014.

(51) Int. Cl.
*A61C 8/00* (2006.01)
*A61L 27/24* (2006.01)
(Continued)

(52) U.S. Cl.
CPC .......... *A61L 27/24* (2013.01); *A61B 17/7032* (2013.01); *A61B 17/7059* (2013.01);
(Continued)

(58) Field of Classification Search
CPC .......... A61L 27/24; A61L 27/06; A61L 27/18; A61L 27/34; A61L 27/3633; A61L 27/54;
(Continued)

(56) References Cited

U.S. PATENT DOCUMENTS 5,152,784 A    10/1992  Tsiibary
5,328,955 A *  7/1994  Rhee ................. A61K 47/48215
                                                    424/422
(Continued)

FOREIGN PATENT DOCUMENTS

EP      1961433      8/2008
WO    WO0064504     11/2000
WO    WO2006047310   5/2006

OTHER PUBLICATIONS

Morra, M. et al, "Collagen I-coated titanium surfaces: mesenchymal cell adhesion and in vivo evaluation in trabecular bone implants", Journal of Biomedical Materials Research, Part A, 78A:3:449-458, XP055185909, (Sep. 1, 2006).

*Primary Examiner* — Nicholas D Lucchesi
(74) *Attorney, Agent, or Firm* — McHale & Slavin, P.A.

(57) ABSTRACT

The invention herein relates to the field of attaching and securing manmade material onto or into bone in correcting bone defects by implanting stress-bearing bone replacements. In particular, the invention relates to applying a coating of collagen securely onto the implant to ensure the collagen material will not be removed from the implant during installation, such as screwing the anchor into the bone. This addresses the removal of the coatings by the scraping action of the bone on the soft collagen. In the past, it has not been possible to provide adequate adhesive strength to the bone collagen/implant interface or the cohesive force of the collagen itself to prevent the removal of the coating by the abrasive action between bone and known implants.

19 Claims, 3 Drawing Sheets

(51) Int. Cl.

| | | |
|---|---|---|
| *A61L 27/54* | (2006.01) | |
| *A61L 27/34* | (2006.01) | |
| *A61F 2/32* | (2006.01) | |
| *A61B 17/80* | (2006.01) | |
| *A61B 17/70* | (2006.01) | |
| *A61B 17/86* | (2006.01) | |
| *A61L 31/04* | (2006.01) | |
| *A61L 31/10* | (2006.01) | |
| *A61L 31/16* | (2006.01) | |
| *A61L 27/56* | (2006.01) | |
| *A61L 31/14* | (2006.01) | |
| *A61L 27/06* | (2006.01) | |
| *A61C 8/02* | (2006.01) | |
| *A61L 27/18* | (2006.01) | |
| *A61L 27/36* | (2006.01) | |
| *A61F 2/30* | (2006.01) | |

(52) U.S. Cl.
CPC ............ *A61B 17/80* (2013.01); *A61B 17/866* (2013.01); *A61C 8/0006* (2013.01); *A61C 8/0013* (2013.01); *A61F 2/32* (2013.01); *A61L 27/06* (2013.01); *A61L 27/18* (2013.01); *A61L 27/34* (2013.01); *A61L 27/3633* (2013.01); *A61L 27/54* (2013.01); *A61L 27/56* (2013.01); *A61L 31/044* (2013.01); *A61L 31/10* (2013.01); *A61L 31/146* (2013.01); *A61L 31/16* (2013.01); *A61F 2002/30062* (2013.01); *A61F 2310/00976* (2013.01); *A61F 2310/00982* (2013.01); *A61L 2300/406* (2013.01); *A61L 2300/414* (2013.01); *A61L 2420/08* (2013.01); *A61L 2430/02* (2013.01); *A61L 2430/12* (2013.01); *A61L 2430/38* (2013.01)

(58) Field of Classification Search
CPC ........ A61L 27/56; A61L 31/044; A61L 31/10; A61L 31/146; A61L 31/16; A61L 2300/406; A61L 2300/414; A61L 2420/08; A61L 2430/02; A61L 2430/12; A61L 2430/38; A61C 8/0006; A61C 8/0013; A61F 2/32; A61F 2002/30062; A61F 2310/00976; A61F 2310/00982; A61B 17/7032; A61B 17/7059; A61B 17/80; A61B 17/866
See application file for complete search history.

(56) References Cited

U.S. PATENT DOCUMENTS

| | | | |
|---|---|---|---|
| 9,186,432 B2 | 11/2015 | Mazzocca et al. | |
| 2007/0077267 A1* | 4/2007 | Molz, IV | A61L 27/227 424/423 |
| 2007/0281024 A1* | 12/2007 | Lautenbach | A61K 9/0004 424/473 |
| 2008/0306554 A1* | 12/2008 | McKinley | A61B 17/866 606/301 |
| 2009/0202608 A1* | 8/2009 | Alessi | A61K 9/0004 424/424 |
| 2010/0003638 A1* | 1/2010 | Collins | A61C 8/0012 433/174 |
| 2010/0092566 A1* | 4/2010 | Alessi | A61K 9/0004 514/1.1 |
| 2011/0054630 A1 | 3/2011 | Shoji | |
| 2011/0150963 A1* | 6/2011 | Clineff | A61L 27/46 424/423 |
| 2011/0262486 A1* | 10/2011 | Tsai | A61K 33/24 424/400 |
| 2012/0171354 A1* | 7/2012 | O'Neill | A61L 27/34 427/2.25 |
| 2012/0316646 A1* | 12/2012 | Gretzer | A61L 27/24 623/16.11 |
| 2013/0197660 A1* | 8/2013 | Bollati | A61L 27/20 623/23.57 |
| 2013/0202670 A1* | 8/2013 | Darmoc | A61L 27/40 424/405 |
| 2015/0231062 A1* | 8/2015 | Lautenbach | A61K 9/0004 29/888.02 |

* cited by examiner

COLLAGEN PERMEATED MEDICAL IMPLANTS

FIELD OF INVENTION

The present invention generally relates to medical implants, and more particularly to medical implants coated with a collagen coating to promote healing and bone ingrowth.

BACKGROUND INFORMATION

A normal human spine is segmented with seven cervical, twelve thoracic and five lumbar segments. The lumbar portion of the spine resides on the sacrum, which is attached to the pelvis. The hips and leg bones support the pelvis. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The, anulus of the disc forms the disc perimeter, and is a tough, outer fibrous ring that binds adjacent vertebrae together. The fiber layers of the anulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases, it is desired to fuse the adjacent vertebrae together after removal of the disc, sometimes referred to as "intervertebral fusion" or "interbody fusion." In this process, spondylodesis or spondylosyndesis is used to join two or more vertebrae to eliminate pain caused by abnormal motion, degradation, fractures or deformities of the vertebrae.

Spinal plates have become one common approach to attaching one adjacent vertebra to another. A spinal plate generally includes an elongated plate of a metal such as titanium or stainless steel. The plate includes a plurality of apertures positioned to allow a surgeon to attach the plate across at least two vertebras with screws. The combination of the plate and screws serve to hold the adjacent vertebra together while the intervertebral fusion occurs.

Biomaterials have been used as implants in the field of spine, orthopedics and dentistry including trauma, fracture repair, reconstructive surgery and alveolar ridge reconstruction for over a century. Although metal implants, such as titanium, have been the predominant implants of choice for these types of load-bearing applications, additional ceramics, non-resorbable polymeric and bioresorbable materials have been employed within the last twenty-five years due to their biocompatibility and physical properties.

Polyetheretherketone (PEEK) is a biomaterial often used in medical implants. For example, PEEK can be molded into preselected shapes that possess desirable load-bearing properties. PEEK is a thermoplastic with excellent mechanical properties, including a Young's modulus of about 3.6 GPa and a tensile strength of about 100 MPa. PEEK is semi-crystalline, melts at about 340 degree C., and is resistant to thermal degradation. Such thermoplastic materials, however, are not bioactive, osteoproductive, or osteoconductive.

Biodegradeable graft fixation anchors and screws are made of Biphasic calcium phosphate poly(L-lactide-co-D, L-lactide). Biodegradable polymeric materials such as poly-lactide and polyglycolide have been used in orthopedic applications for decades. These components are designed to be degraded in the body.

Therefore, there is a need for a series of orthopedic implants, which combine a biocompatible and or biodegradable material or polymer such as, but not limited to, titanium or PEEK or any other material suitable for implantation within an animal in vivo combined with collagen. The collagen should be applied to the implant or the implant should include geometry that allows the implant to be inserted without scraping away the coating. In addition, the collagen coating could provide a lattice for bone in-growth into a portion of the implant to integrate the implant into the bone of the patient or replace the implant with bone as it is absorbed.

SUMMARY OF THE INVENTION

Briefly, the invention herein relates to the field of attaching and securing manmade material onto or into bone in correcting bone defects by implanting stress-bearing bone replacements. In particular, the invention relates to applying collagen securely onto or into the implant to ensure the collagen material will not be removed from the implant during installation such as screwing the anchor into the bone. This addresses the removal of the coatings by the scraping action of the bone on the soft collagen. In the past, it has not been possible to provide adequate adhesive strength to the bone collagen/implant interface or the cohesive force of the collagen itself to prevent the removal of the coating by the abrasive action between bone and known implants.

The use of coating the prosthesis or implantables with a material which is known to encourage bone growth, such as collagen or collagen plus halyuranic acid or growth hormones, proteins or stimulators in collagen are beneficial to creating a suitable environment for the implant to function as intended by creating the needed bone growth to support or replace the implant.

The use of stress-bearing materials for bone replacement is well known. A large number of designs have been used to replace missing or diseased portions of the bone structure that are stress-bearing, such as bone shafts, joints, and tooth roots. These designs include artificial shafts and joints, and associated devices intended to mimic the functionality of the human skeletal system.

More commonly, however, shafts or other prostheses constructed of metal or metal alloys have been used as the stress-bearing portion of the bone replacement. Such metal pins, screws or artificial joints are constructed of suitable inert metals such as titanium, stainless steels, other alloys such as cobalt, chromium and molybdenum alloys. The metallic pin or joint is sometimes provided with an oxide coating in order to prevent corrosion and instability.

It has been observed in the use of such metallic implants, that it is frequently necessary to provide a mechanism to prevent the shifting of the implant in place and to fix its position with respect to adjacent bone. Instead of a cement to secure the implant, the present invention places the collagen on the implant to encourage the bone to grow into the small spaces, and add additional bone in the immediate area to provide additional strength. The collagen and any additives may be applied to the implant in a solid or liquid form by the processes of spraying, dipping, brushing or electrostatic application.

It is clear from present experience that an implanted stress-bearing prosthesis should be provided with a means to assure permanent attachment of the prosthesis to the remaining portions of the skeletal system; ideally, it should be provided with a fixative that encourages the surrounding bone to intrude into the porous surface of the implant. The present invention provides an effective and satisfactory form of fixation.

Thus, the invention provides a device and method for providing a collagen containing medical implant. The device includes a medical implant impregnated with a collagen coating. The implant may be constructed of any biologically compatible material suitable for use as a bone stabilizer or replacement. The collagen may be applied by spraying, brushing, dipping, or the like.

Accordingly, it is an objective of the present invention to provide a collagen containing medical implant.

It is a further objective of the present invention to provide a method of infusing a medical implant with a collagen.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1:
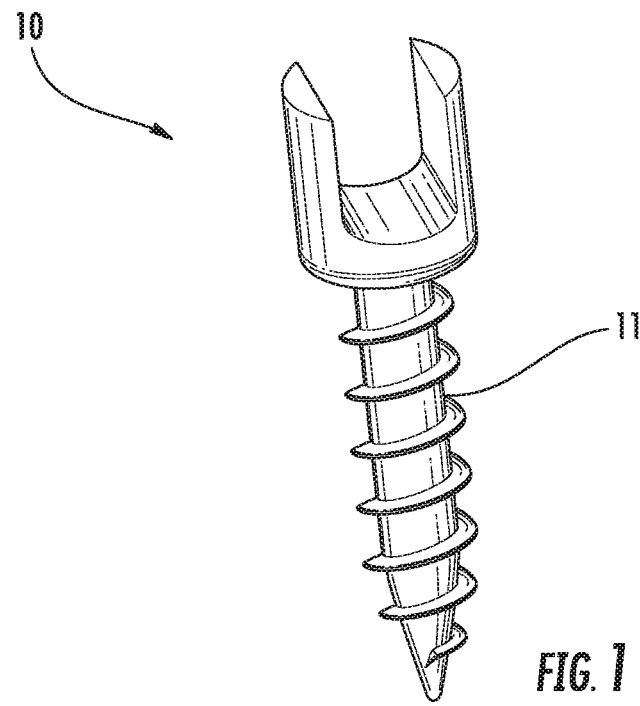
FIG. 1 is a top perspective view of one embodiment of the present invention.
Figure 2:
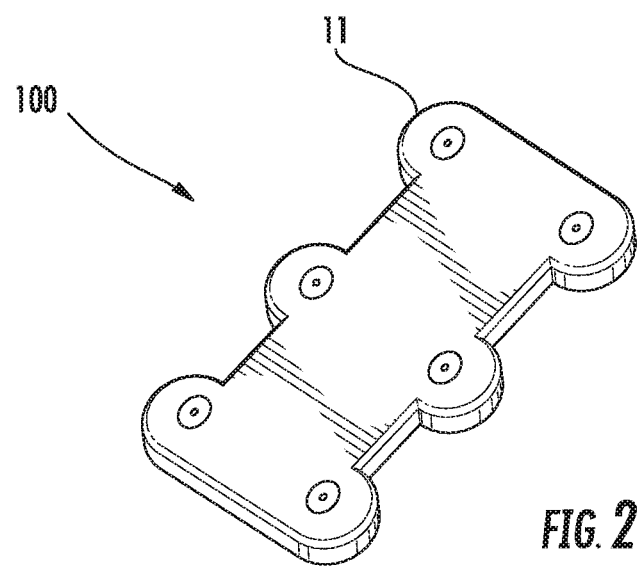
FIG. 2 is top perspective view of an alternative embodiment of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to FIGS. 1-6, a collagen coated implant 10, 100 and system for coating an implant with a collagen coating 11 is illustrated. The device 10, 100 includes an implant for implantation as a bone replacement that comprises a stress-bearing member containing sterile non-immunogenic collagen 11. The implants illustrated herein are a pedicle screw 10 and a bone plate 100. However, it should be noted that while the spinal implants are illustrated, the present invention may be applied to any type of stress bearing implant such as, but not limited to, hip implants, dental implants, long bone fixation, bone nails, pins, bone screws, sutures and the like without departing from the scope of the invention. The preferred collagen coating/infusion of the present invention is advantageously an atelopeptide form of xenogeneic, autogeneic or autologous origin. Accordingly, the xenogeneic aspect of the collagen provided in the invention is intended to indicate that the majority of the material can be of foreign species origin and includes such materials that may contain some percentage of autogenous material.

In other aspects, the invention relates to a method of placing, transporting and delivering adequate collagen below the bone surface, next to the implant, to promote bone growth in the region of the implant or replacement of the implant.

Collagen refers to collagen that has been disassembled into individual triple helical molecules with or without their telopeptide extensions and brought into solution, and then regrouped into fibrillar, open cell or sheet form. In this form, the fibrils consist of long thin collagen molecules staggered relative to one another, as milled material from scaffolds, or sponges of DHT cross-linked, or simple lyophilized or dried biological material including fibrin or adhesives. Alternatively, the collagen may be applied as a liquid then dried while already placed on the implant. It can be prepared in freeze-dried form and sterilized by irradiation or heat. It should thus be appreciated that the collagen can be in a liquid or a solid form by several processes including, but not limited to, spraying, brushing, dipping or electrostatic attraction.

The prostheses of the invention comprise an implant 10, 100 with a form of collagen 11 with the required properties of sterility and non-immunogenicity. The implants ability to hold and deliver the collagen to the bone implant interface constitutes the invention, and any conventionally used or operable stress-bearing prosthesis, anchor, attachment or screw can be used. Such items are ordinarily metallic, ceramic or polymeric, and may be provided with porous surfaces by suitable techniques known in the art. They are of such design and material as to be appropriate to their intended use, which may include replacement of diseased bone, correction of defects, or anchoring teeth.

The requirements for the collagen preparation used to coat the stress-bearing member are merely that the collagen 11 be a non-immunogenic, which is uncontaminated and which is sterile so as not to produce infection. Sterilization can be accomplished by a variety of means including, for example, heat, irradiation, or, if the preparation is reconstituted, by sterile filtration of the collagen while it is still in solution. Sterilization by heat or irradiation may cause degradation or cross-linking; however, it is not clear that these results will have a negative impact on the efficacy of the resulting preparation. Accordingly, any method of sterilization suitable for the preparation used is satisfactory.

Figure 3:
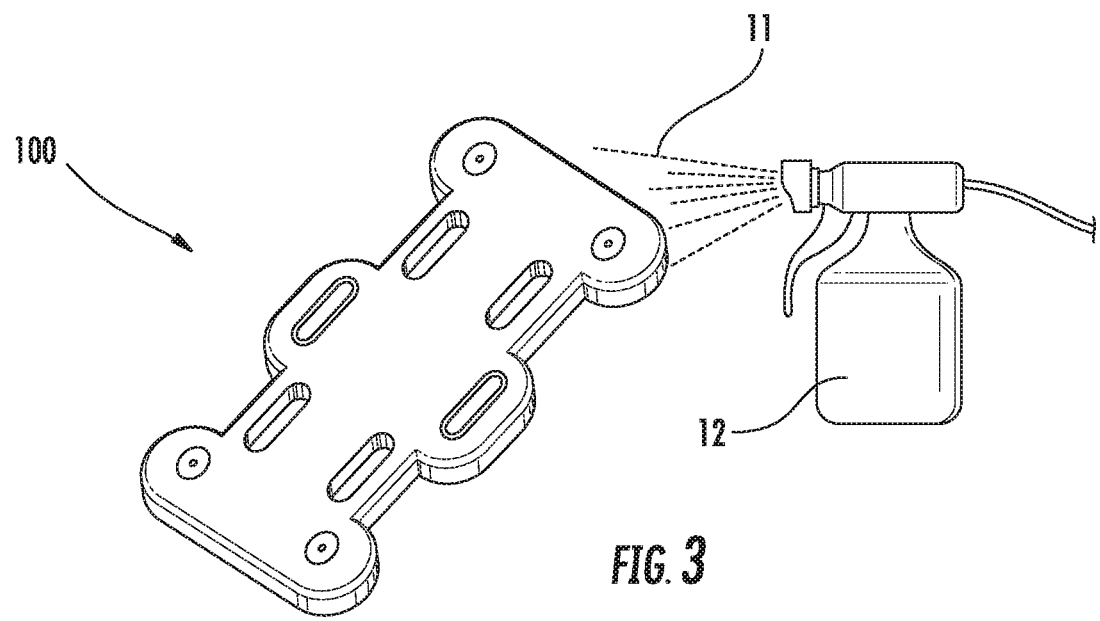
FIG. 3 is a top perspective view of the embodiment shown in FIG. 2 illustrating the spray method of applying collagen coating to the medical implant.
Figure 4:
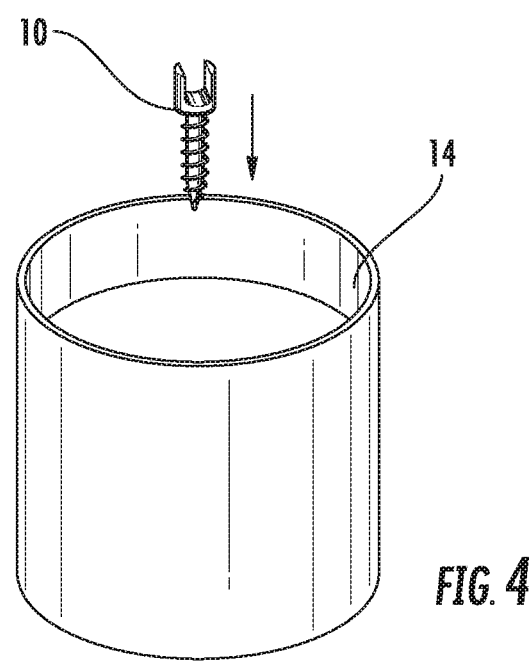
FIG. 4 is a top perspective view of the embodiment shown in FIG. 1 illustrating the dipping method of applying collagen coating to the medical implant.

Of course, it is not necessary that all of the collagen 11 used to coat the prosthesis be of one type of preparation. Accordingly, mixtures in any proportion of the foregoing purified collagen preparations or other collagen preparations, which meet the required specifications of being non-immunogenic, and sterile, can be used. The proportions are not critical and can be adjusted to suit the desired physical properties of the coating. For example, FIG. 3 illustrates one method of applying the collagen to the implant 100. In this method, the collagen is applied using a spray process 12. The spray may be provided using a compressed air method or an airless method without departing from the scope of the invention. FIG. 4 illustrates an alternative method of applying collagen coating to the implant 10. This method involves dipping the implant into a container 14 containing the collagen 11. An aid to infusing the device with collagen is by submersing the device completely in a closed system and then applying a vacuum. This will remove the air from the cavities and allow it to be replaced with the collagen solution. If additional collagen is required, the process may be repeated by drying. This process may be repeated until the voids will not accept more solution or suspension. Surface structure modifications may be utilized for providing sufficient collagen to fill the gaps between implant and host bone, while also delivering sufficient collagen to the bone implant area. Such surface modifications may include, but should not be limited to, bead blasting, sand blasting, etching, casting, knurling, machining and the like.

Figures 5A, 5B:
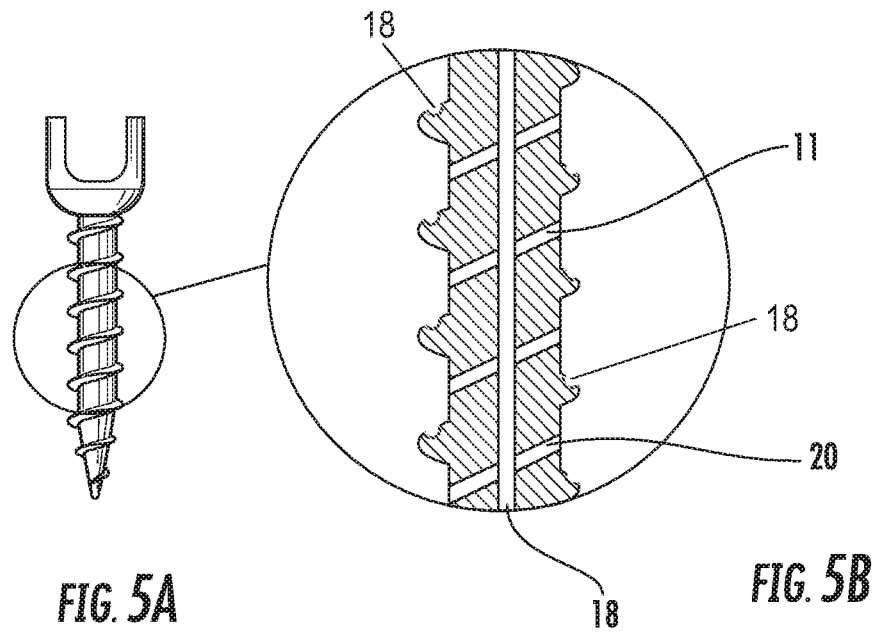
FIG. 5A is a side view of the embodiment illustrated in FIG. 1.
FIG. 5B is a partial section view taken along lines 5-5 of FIG. 5A illustrating a cannulated system with weep holes for distribution of the collagen coating material.
Figure 6:
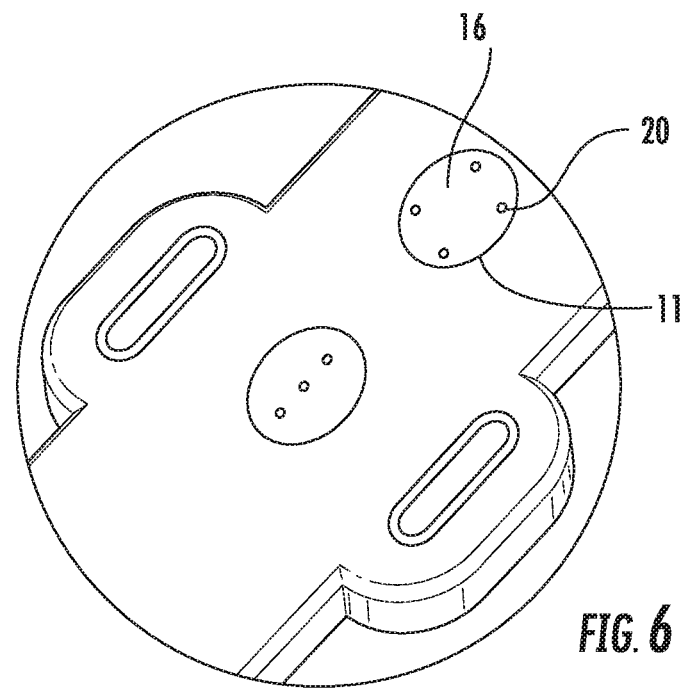
FIG. 6 is a partial perspective view of a reservoir with weep holes for distribution of the collagen coating material.

Referring to FIGS. 5 and 6, a modified implant is illustrated. The implant 10, 100 is modified to provide cavities 16 or channels 18 of sufficient size and depth to act as pockets that position the collagen below the abrasive surface of the bone. The pockets or channels may be made by coarse etching of the implant surface, drilling, molding or machining the pockets into the implant material. The cavity 16 or channel 18 may be a central cavity with delivery holes 20 in the area the collagen is needed, or the cavity can be a spiral channel. The channel, if a spiral such as threads, may have the leading edge of the groove higher than the trailing edge to avoid removing the collagen by the act of screwing the implant into place. If the leading edge of the spiral is lower than the trailing edge when the item is screwed into the bone, the implant may act as a drill bit and remove the collagen as bone material fills the groove and push the collagen out.

The efficacy of the coating in encouraging suitable bone growth into the surface of the prosthesis may be either conductive or inductive depending on the nature of the collagen preparation used and whether or not it contains additional proteins, such as those normally characterized as osteogenesis factors.

Conductive bone growth refers to a process for encouraging bone growth, which involves the metabolism of previously, committed osteoprogenitor cells; and these cells directly affect the osteogenesis. Ordinarily, this can occur by providing a matrix into which the new bone can conveniently grow. Inductive bone growth further includes the step of converting previously uncommitted cells to osteogenic ones. The precise nature of this process is not known, but it is understood that it is mediated by proteins found ordinarily in bone. If desired, the collagen coating of the prosthesis may include such factors, and in this case, bone growth will be considered inductive, though induction includes the conductive process supported by the matrix provided by the collagen. It should also be noted that other types of bone growth accelerants, drugs or any material that has an effect via chemical or metabolic means (immediate release or extended release), biologics, antibiotics for infection control or the like may also be added to the collagen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention, and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A collagen containing medical implant assembly comprising:

a bone implant for implantation as an in vivo bone replacement, said implant being constructed and arranged to hold and deliver a non-immunogenic and sterile collagen coating to a bone implant interface, said bone implant including modifications to it's outer surface for containing a portion of said collagen coating, said modifications to said outer surface include a spiral channel, said spiral channel is provided in the form of threads, said threads having a thread groove with a leading edge higher than a trailing edge to avoid removing the collagen by the act of screwing said bone implant into place, said implant having a collagen coating on at least a portion of said implant prior to implantation, said collagen coating secured to said spiral channel of said medical implant, said modifications to said outer surface allow said collagen coating to be positioned below an abrasive outer surface of a bone to which said bone implant is secured, said spiral channel constructed and arranged so as to not contact the bone during in vivo bone replacement implantation, said collagen coating being non-immunogenic and sterile.

2. The collagen containing bone implant of claim 1 wherein said bone implant is at least partially porous whereby a portion of said collagen coating is stored below said outer surface of said bone implant, said collagen coating positioned below said outer surface of said bone implant being free to migrate to said outer surface.

3. The collagen containing bone implant of claim 1 wherein said collagen coating is an atelopeptide form of xenogeneic collagen.

4. The collagen containing bone implant of claim 1 wherein said collagen coating is an atelopeptide form of autologous collagen.

5. The collagen containing bone implant of claim 1 wherein said collagen coating includes more than one type of collagen in a mixture.

6. The collagen containing bone implant of claim 1 wherein said collagen coating is prepared by being disassembled into individual triple helical molecules with their telopeptide extensions and brought into solution, and then regrouped into fibrillar form.

7. The collagen containing bone implant of claim 1 wherein said collagen coating is prepared by being disassembled into individual triple helical molecules without their telopeptide extensions and brought into solution, and then regrouped into fibrillar form.

8. The collagen containing bone implant of claim 1 wherein said collagen coating is a collagen scaffold, said scaffold stripped of collagen cells but still containing growth factors from said collagen.

9. The collagen containing bone implant of claim 1 wherein said collagen coating being applied to said outer surface of said bone implant as dried biological material.

10. The collagen containing bone implant of claim 9 wherein said collagen coating includes adhesive for adhering said dried biological material to said outer surface of said bone implant.

11. The collagen containing bone implant of claim 10 wherein said adhesive is fibrin.

12. The collagen containing bone implant of claim 1 wherein said collagen coating being applied to said outer surface of said bone implant as liquid biological material.

13. The collagen containing bone implant of claim 1 wherein said bone implant includes a central cavity having at least one delivery hole sized to allow flow of said collagen coating from said central cavity to a bone to a bone implant interface.

14. The collagen containing bone implant of claim 1 wherein said collagen coating includes additional proteins to encourage bone growth.

15. The collagen containing bone implant of claim 14 wherein said additional proteins are those normally characterized as osteogenesis factors.

16. The collagen containing bone implant claim 1 wherein said bone implant is constructed from a bioresorbable material.

17. The collagen containing bone implant of claim 1 wherein said implant is a bone screw.

18. The collagen containing bone implant of claim 17 wherein said bone screw is a pedicle screw.

19. The collagen containing bone implant of claim 1 wherein said collagen coating includes antibiotics.

* * * * *